United States Patent
Cho et al.

(10) Patent No.: US 9,109,983 B2
(45) Date of Patent: Aug. 18, 2015

(54) APPARATUS FOR MEASURING IMPACT ABSORPTION RATE OF IMPACT ABSORPTION MEMBER

(71) Applicants: Daihan Cho, Yongin (KR); Kyoungwoo Park, Yongin (KR)

(72) Inventors: Daihan Cho, Yongin (KR); Kyoungwoo Park, Yongin (KR)

(73) Assignee: SAMSUNG DISPLAY CO., LTD., Yongin, Gyunggi-Do (KR)

( * ) Notice: Subject to any disclaimer, the term of this patent is extended or adjusted under 35 U.S.C. 154(b) by 247 days.

(21) Appl. No.: 13/756,649

(22) Filed: Feb. 1, 2013

(65) Prior Publication Data

US 2013/0205868 A1 Aug. 15, 2013

(30) Foreign Application Priority Data

Feb. 9, 2012 (KR) .......................... 10-2012-0013431

(51) Int. Cl.
*G01N 3/30* (2006.01)
*G01M 7/08* (2006.01)
*G01L 5/00* (2006.01)

(52) U.S. Cl.
CPC .............. *G01N 3/30* (2013.01); *G01L 5/0052* (2013.01); *G01M 7/08* (2013.01)

(58) Field of Classification Search
CPC ........... G01N 3/30; G01N 3/303; G01N 3/34; G01N 3/342; G01N 3/48; G01L 5/0052; G01M 7/08

USPC ............. 73/12.01, 12.06, 12.13, 78, 82, 866, 73/865.9

See application file for complete search history.

(56) References Cited

U.S. PATENT DOCUMENTS

| | | | | |
|---|---|---|---|---|
| 4,640,120 | A * | 2/1987 | Garritano et al. | 73/12.13 |
| 6,523,391 | B1 * | 2/2003 | Knox et al. | 73/12.06 |
| 2004/0200264 | A1 * | 10/2004 | Chen et al. | 73/12.06 |
| 2005/0016256 | A1 * | 1/2005 | Ishikawa | 73/12.13 |
| 2006/0005606 | A1 * | 1/2006 | Hatanaka et al. | 73/12.14 |
| 2009/0019917 | A1 * | 1/2009 | Lim et al. | 73/12.06 |
| 2009/0165532 | A1 * | 7/2009 | Yee et al. | 73/12.09 |
| 2009/0235718 | A1 * | 9/2009 | Fox | 73/12.06 |
| 2011/0120210 | A1 * | 5/2011 | Saitoh et al. | 73/12.06 |
| 2012/0006125 | A1 * | 1/2012 | Wen | 73/788 |

FOREIGN PATENT DOCUMENTS

| | | | |
|---|---|---|---|
| KR | 10-2006-0057072 A | 5/2006 | |
| KR | 10-2007-0019060 A | 2/2007 | |
| KR | 10-2009-0086723 A | 8/2009 | |

* cited by examiner

*Primary Examiner* — Lisa Caputo
*Assistant Examiner* — Philip Cotey
(74) *Attorney, Agent, or Firm* — Lee & Morse, P.C.

(57) ABSTRACT

An impact absorption rate measuring apparatus includes a measuring unit configured to support an impact absorption member and to measure an impact absorption rate of the impact absorption member, an impact conversion member on the impact absorption member, the impact absorption member being stacked between the measuring unit and the impact conversion member, and a fall member configured to fall on an upper surface of the impact conversion member, the upper surface of the impact conversion member facing away from the impact absorption member.

20 Claims, 10 Drawing Sheets

APPARATUS FOR MEASURING IMPACT ABSORPTION RATE OF IMPACT ABSORPTION MEMBER

CROSS-REFERENCE TO RELATED APPLICATIONS

A claim for priority under 35 U.S.C. §119 is made to Korean Patent Application No. 10-2012-0013431, filed Feb. 9, 2012, the entirety of which is incorporated by reference herein.

BACKGROUND

The inventive concepts described herein relate to an apparatus measuring an impact absorption rate of an impact absorption member, and more particularly, to an impact absorption rate measuring apparatus inserted in a display apparatus.

Figure 1:
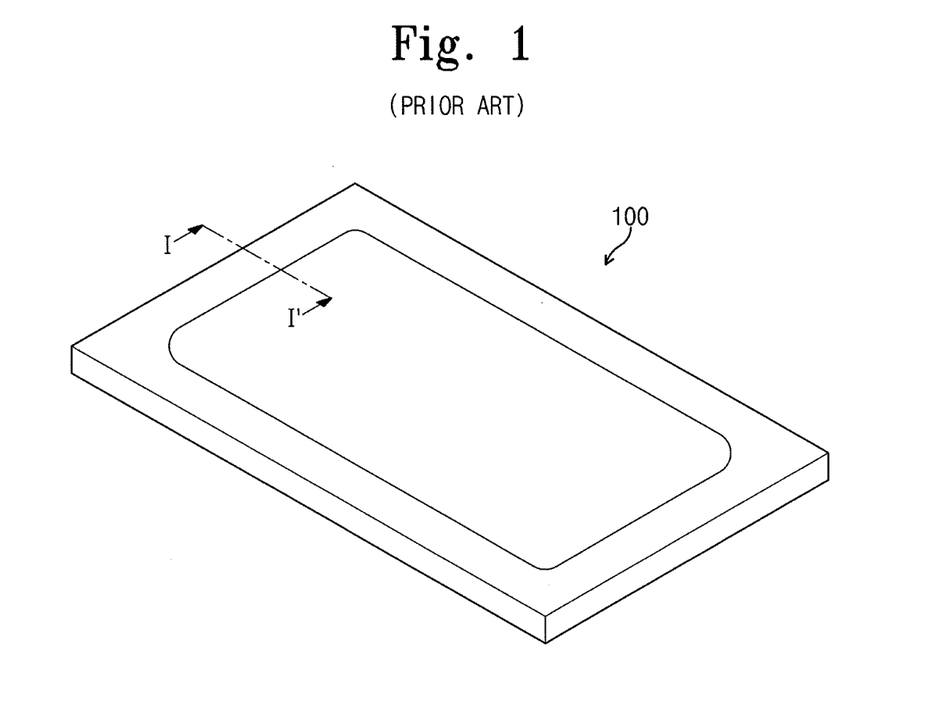
FIG. 1 is a perspective view of a flat display device.
Figure 2:
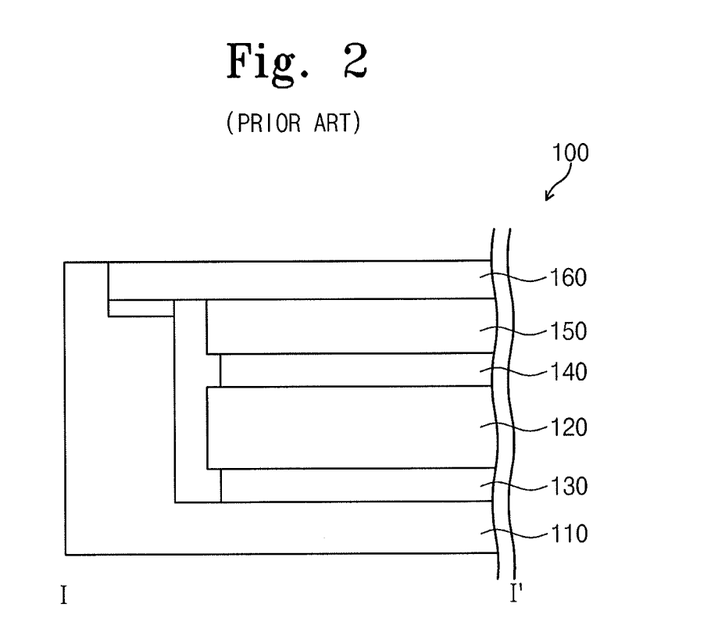
FIG. 2 is a cross-sectional view taken along line I-I' of FIG. 1.

As illustrated in FIGS. 1 and 2, a flat display device 100 may include a display panel 120 provided within a chassis 110. The flat display device 100 may further include a polarization plate 140 and a functional member, e.g., a window 160, in addition to the display panel 120. The flat display device 100 may further include at least one impact absorption member, e.g., an adhesive sheet 150 uniting members and/or a cushion sheet 130 absorbing an external impact.

The flat display device of FIGS. 1 and 2 may be any suitable display. For example, the flat display device 100 may be a liquid crystal display device, and may further include a back-light unit providing a light to the display panel 120.

The flat display device 100 may include the impact absorption member, regardless of the type of the display device. The flat display device 100 may have the impact absorption member for protecting constituent elements from an external impact. It is important to select the impact absorption member to make a slim flat display device and to protect the flat display device from an external impact.

After making a flat display device, an impact absorption rate of the flat display device may be measured. For example, an impact absorption rate may be measured by dropping the flat display device. The same test may be executed with respect to flat display devices adopting different impact absorption members, and an optimum impact absorption member may be decided according to the test results.

However, when the impact absorption rate is measured by dropping the flat display device, it may be difficult to directly measure an impact absorption rate of the impact absorption member. For example, if a test is iteratively executed with flat display devices having different impact absorption members, a difference may be generated in the test results due to differences of the flat display devices, regardless of the impact absorption members. For example, different test results may be caused according to display parts (e.g., corner, display surface, etc.) contacting a reference surface (e.g., the ground).

SUMMARY

One aspect of embodiments of the inventive concept is directed to provide an impact absorption rate measuring apparatus, including a measuring unit configured to support an impact absorption member and to measure an impact absorption rate of the impact absorption member, an impact conversion member on the impact absorption member, the impact absorption member being stacked between the measuring unit and the impact conversion member, and a fall member configured to fall on an upper surface of the impact conversion member, the upper surface of the impact conversion member facing away from the impact absorption member.

The measuring unit may include first member configured to support the impact absorption member, a sensor configured to calculate the impact absorption rate, and a second member configured to support the sensor, the sensor being between the first member and the second member along a vertical direction.

The measuring unit may further include a plurality of protrusion portions spaced apart from each other, the protrusion portions extending from the second member to the first member.

The plurality of protrusion portions may be spaced apart from each other at a constant interval, the sensor being placed between the protrusions along a horizontal direction.

The plurality of protrusion portions may be spaced apart from each other along a perimeter of the first member to define an outline, the sensor being in a center of the outline.

The first member may include a plurality of groove portions, the protrusion portions being partially inserted into the groove portions, respectively.

The impact absorption rate measuring apparatus may further include a plurality of receiving members on a surface of the first member facing the second member, the protrusion portions being partially inserted into grooves in the receiving members, respectively.

The sensor may be configured to measure an impact power and an impact time to calculate the impact absorption rate.

The sensor may be configured to calculate the impact absorption rate according to the following equation, $$Ir = \frac{Ddt}{Idt} \times \left\{ \frac{(Iif - Dif)}{Iif} \times 100 \right\},$$

wherein Ir is the impact absorption rate, Ddt is an impact time measured when the impact absorption member is not disposed, Idt is an impact time measured when the impact absorption member is disposed, Iif is an impact power measured when the impact absorption member is not disposed, and Dif may be an impact power measured when the impact absorption member is disposed.

The impact conversion member may include metal.

The fall member may have a shape configured to force an impact to the impact conversion member from a point.

The fall member may have a spherical shape or a hemispherical shape.

The impact absorption rate measuring apparatus may further include a fixing member configured to temporarily fix the fall member at an upper side of the impact absorption member.

The fixing member may include a vertical axis portion perpendicular to the measuring unit, a parallel axis portion attached to the vertical axis portion at an upper side of the measuring unit to be parallel with the measuring unit, and a magnet portion attached to the parallel axis portion and fixing the fall member.

Another aspect of embodiments of the inventive concept is directed to provide an impact absorption rate measuring apparatus, including a first member supporting an impact absorption member, an impact conversion member disposed on the impact absorption member, a fall member configured to free fall on the impact conversion member, and a sensor disposed at a lower side of the first member, the sensor being configured to measure an impact absorption rate of the impact absorption member.

The impact absorption rate measuring apparatus may further include a second member, the sensor being between the first and second members.

The sensor may be configured to measure an impact power forced to the first member from the fall member and an impact time when the fall member forces an impact to the first member, and to calculate the impact absorption rate based on the impact power and the impact time.

BRIEF DESCRIPTION OF THE FIGURES

The above and other objects and features will become apparent from the following description with reference to the following figures, in which.

DETAILED DESCRIPTION

The inventive concept is described more fully hereinafter with reference to the accompanying drawings, in which embodiments of the inventive concept are shown. This inventive concept may, however, be embodied in many different forms and should not be construed as limited to the embodiments set forth herein. Rather, these embodiments are provided so that this disclosure will be thorough and complete, and will fully convey the scope of the inventive concept to those skilled in the art. In the drawings, the size and relative sizes of layers and regions may be exaggerated for clarity. Like reference numerals refer to like elements throughout.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the inventive concept.

Spatially relative terms, such as "beneath", "below", "lower", "under", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" or "under" other elements or features would then be oriented "above" the other elements or features. Thus, the exemplary terms "below" and "under" can encompass both an orientation of above and below. The device may be otherwise oriented (rotated 90 degrees or at other orientations) and the spatially relative descriptors used herein interpreted accordingly. In addition, it will also be understood that when a layer is referred to as being "between" two layers, it can be the only layer between the two layers, or one or more intervening layers may also be present.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

It will be understood that when an element or layer is referred to as being "on", "connected to", "coupled to", or "between" another element or layer, it can be directly on, connected, coupled, or between the other element or layer, or intervening elements or layers may be present. In contrast, when an element is referred to as being "directly on," "directly connected to", "directly coupled to", or "directly between" another element or layer, there are no intervening elements or layers present.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

Figure 3:
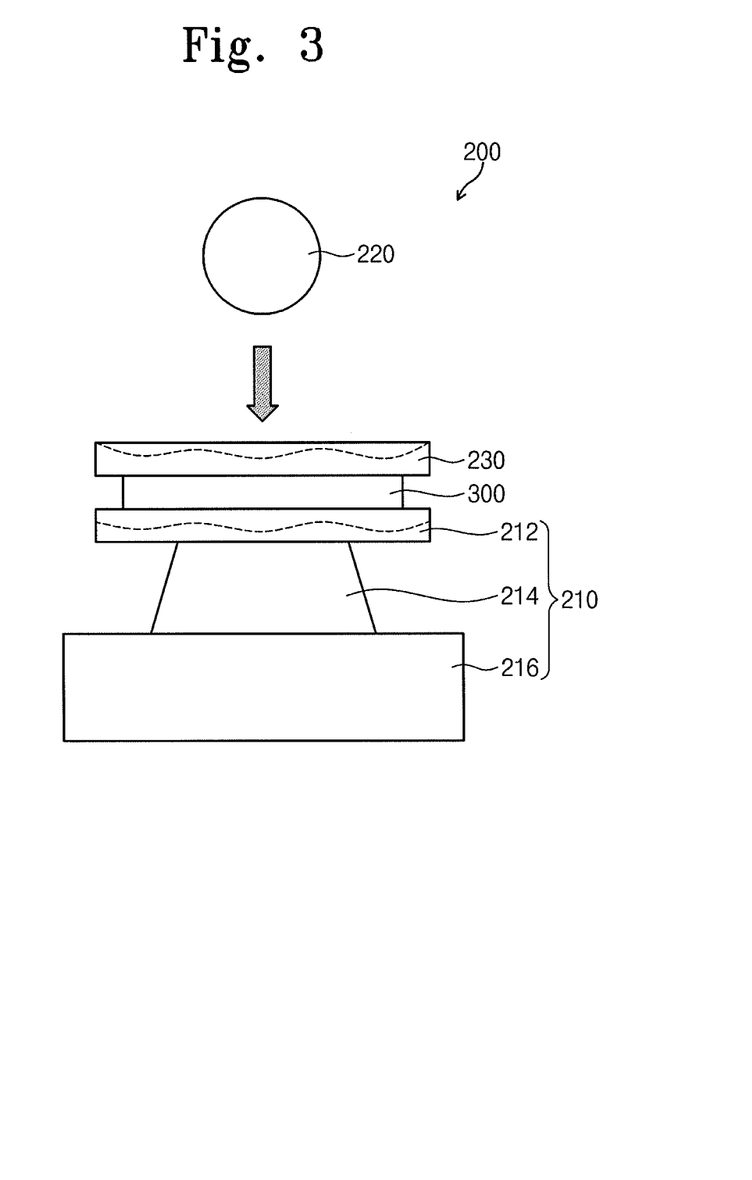
FIG. 3 is a lateral view of an impact absorption rate measuring apparatus according to an embodiment of the inventive concept.
Figure 4:
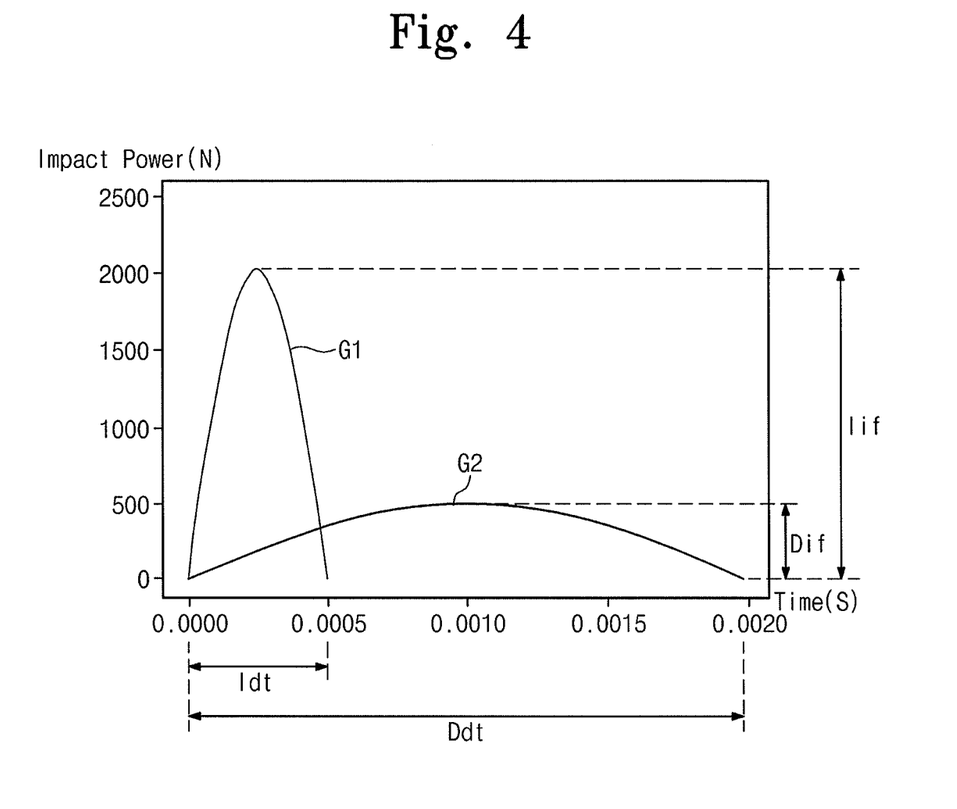
FIG. 4 is a graph illustrating an impact power and an impact time measured by the impact absorption rate measuring apparatus in FIG. 3.

FIG. 3 is a lateral view of an apparatus for measuring an impact absorption rate of an impact absorption material according to an embodiment of the inventive concept. FIG. 4 is a graph describing an impact power and an impact time measured by the apparatus in FIG. 3.

As illustrated in FIG. 3, an impact absorption measuring apparatus 200 (hereinafter, referred to as a measuring apparatus) may include a measuring unit 210 to calculate an impact absorption rate of an impact absorption member 300, a fall member 220 to be dropped on an upper side of the measuring unit 210, and an impact conversion member 230 to be impacted by the fall member 220. The impact absorption member 300 may be positioned between the measuring unit 210 and the impact conversion member 230, and the fall member 220 may be dropped on an upper surface of the impact conversion member 230 covering the impact absorption member 300.

The impact absorption member 300 may be the adhesive sheet 150 and/or the cushion sheet 130 inserted within a flat display device 100 (refer to FIG. 1). The impact absorption member 300 may have inherent elasticity and hardness. The impact absorption member 300 may have an inherent impact absorption rate according to inherent properties of matter, e.g., elasticity, hardness, and the like.

As the display device becomes slim, a thin impact absorption member with a high impact absorption rate may be required. Considering that a specifically developed impact absorption member with a high impact absorption rate may be expensive, an existing impact absorption member suitable for a use in a flat display device may be adopted to reduce costs of the flat display device. The display device may include an organic light emitting display panel susceptible to an external impact. Therefore, according to example embodiments, the impact absorption member 300 may be tested separately from the display device for impact absorption rate in order to evaluate its properties, prior to incorporation thereof into the flat display device 100.

Referring back to FIG. 3, the measuring unit 210 may support the impact absorption member 300, and may measure an impact absorption rate of an external impact. The measuring unit 210 may include a first member 212 supporting the impact absorption member 300, a sensor 214 calculating the impact absorption rate, and a second member 216 opposed to the first member 212. The sensor 214 may be interposed between the first and second members 212 and 216, so the second member 216 may support the sensor 214. As such, the sensor 214, the first member 212, the impact absorption member 300, and the impact conversion member 230 may be sequentially stacked on the second member 216.

For example, the first member 212 and the impact conversion member 230 may be flat-plate shaped and may have sufficiently large sizes to completely overlap the impact absorption member 300. For example, the second member 216, the sensor 214, the first member 212, the impact absorption member 300, and the impact conversion member 230 may be aligned, so centers thereof may be on a same vertical line. As such, a point impact on the impact conversion member 230 may be evenly transformed into a surface contact. An impact absorption rate measuring method of the sensor 214 will be more fully described later.

When the display device 100 falls from a predetermined height, the chassis 110 may crash into a surface or another object, and the impact of the crash forced to the display panel 100 may be partially absorbed by the adhesive sheet 150 and the cushion sheet 130 and partially transferred to other components, e.g., the display panel 120 and the like. At an initial stage of the impact, the impact may be focused on a part of the chassis 110. However, the impact may be spread to the entire display device. The measuring unit 210 according to example embodiments may measure an impact absorption rate of the impact absorption member 300, e.g., the adhesive sheet 150 and/or the cushion sheet 130, used in such display devices.

Referring back to FIG. 3, the impact conversion member 230 may be disposed on the impact absorption member 300, and may convert a point impact forced from the exterior into a surface impact. The surface impact may be transferred to the impact absorption member 300. The impact absorption member 300 may absorb a part of the surface impact. The impact conversion member 230 may provide an actual impact condition when the display device 100 falls.

The impact conversion member 230 may have a function corresponding to the chassis 110 (refer to FIG. 2) of the display device 100. Thus, the measuring apparatus 200 according to the inventive concept may measure an impact absorption rate of the impact absorption member 300 inserted within the display device without a finished display device. Impact absorption rates of different impact absorption members selectively disposed on the measuring unit 210 may be measured, and one of the different impact absorption members may be selected according to a use to be applied to a display device.

For example, the impact conversion member 230 may be formed of metal. In another example, the impact conversion member 230 may be formed of a material applicable to the chassis 110 of the display device 100 other than the metal, e.g., plastic.

The fall member 220 free falls from a predetermined height to force an impact to the impact conversion member 230. The fall member 220 may have a shape forcing an impact to the impact conversion member 230 from a point, so as not to generate a difference according to a test number and so as to force a constant impact. For example, the fall member 220 may have a cylindrical shape, a spherical shape, or a hemispherical shape. In another example, the fall member 220 may have a shape where a cylindrical shape and a hemispherical shape are partially united, e.g., a hemispherical surface of the hemispherical shape and a base side of a cylindrical shape may be united.

An impact absorption rate calculating method of the measuring apparatus 200 according to an embodiment of the inventive concept will be described with reference to FIG. 4.

The sensor 214 may measure an impact power and an impact time to calculate an impact absorption rate. First, the sensor 214 may measure an impact power and an impact time under the condition that the impact conversion member 230 is not positioned, i.e., a "first condition," so the fall member 220 impacts the impact absorption member 300 directly. The impact power and the impact time measured under the first condition are illustrated in graph G1 of FIG. 4. The impact power and the impact time measured under the first condition may be reference data stored in the sensor 214.

The sensor 214 may measure an impact power and an impact time under the condition that the impact conversion member 230 is positioned, i.e., a "second condition," so the fall member 220 impacts the conversion member 230 to transform the point impact into a surface impact with respect to the impact absorption member 300. The impact power and the impact time measured under the second condition are illustrated in graph G2 of FIG. 4.

The impact absorption rate of the impact absorption member 300 may be calculated by the following equation (1).

$$Ir = \frac{Ddt}{Idt} \times \left\{ \frac{(Iif - Dif)}{Iif} \times 100 \right\} \qquad \text{Equation (1)}$$

In Equation (1) above, Ir refers to the impact absorption rate, Ddt refers to an impact time at the first condition, and Idt refers to an impact time at the second condition. Iif refers to an impact power at the first condition, and Dif refers to an impact power at the second condition. The impact power refers to a maximum impact power during the impact time.

Figure 5:
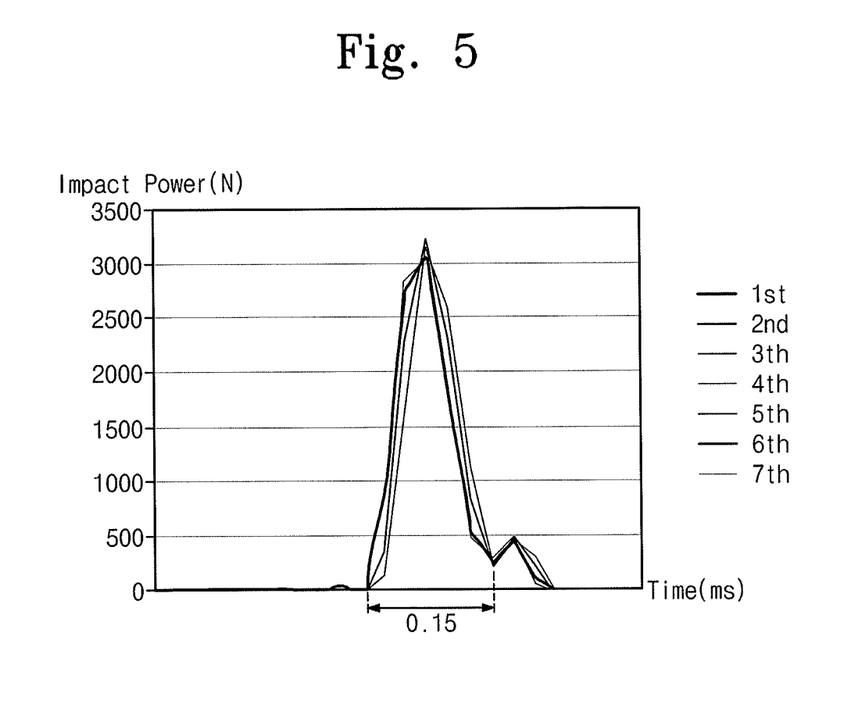
FIG. 5 illustrates graphs obtained by iteratively performing an impact test under a first condition.
Figure 6A:
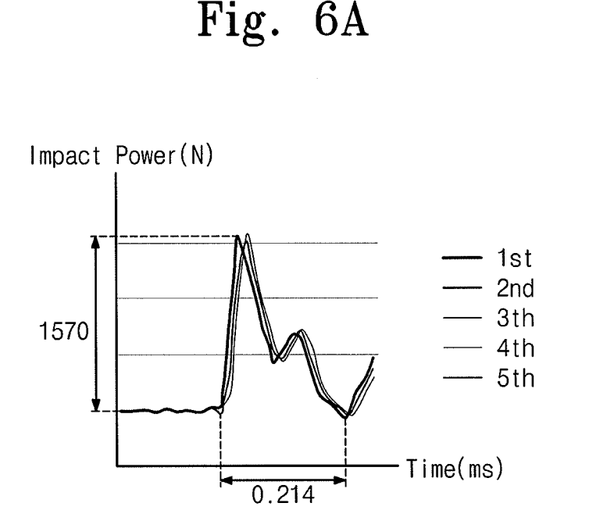
FIGS. 6A to 6C illustrate graphs obtained by iteratively performing an impact test under a second condition.
Figure 6B:
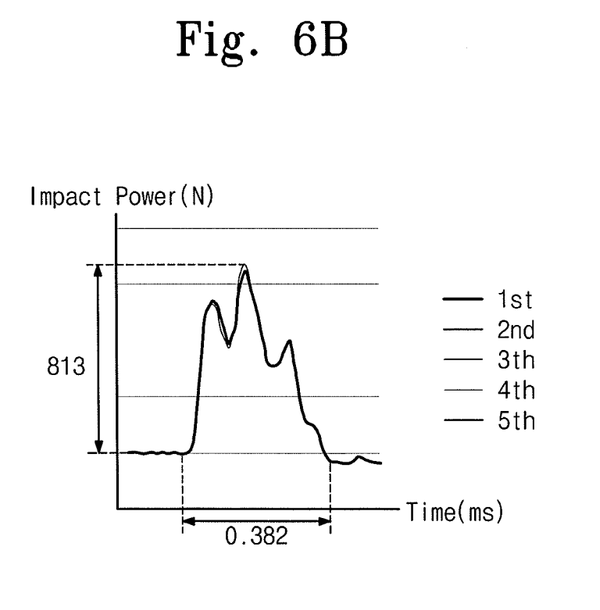
Figure 6C:
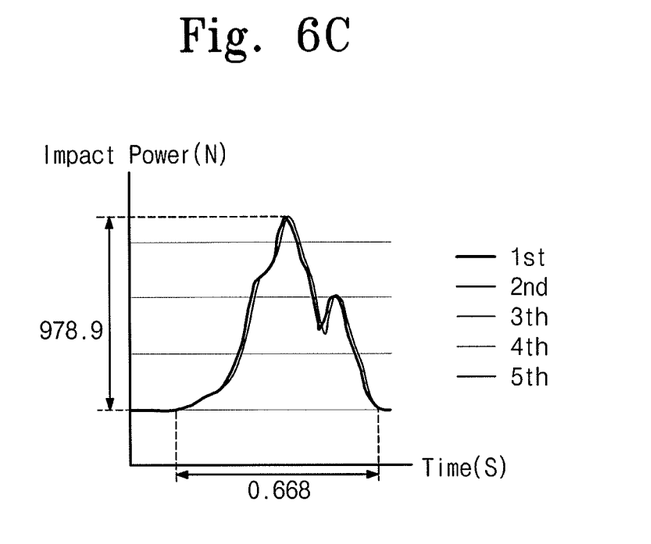

The measuring apparatus 200 according to the inventive concept may obtain a reliable test result of a high impact absorption rate. FIG. 5 illustrates graphs obtained by iteratively performing an impact test under the first condition, and FIGS. 6A to 6C illustrate graphs obtained by iteratively performing an impact test under the second condition. It is noted that different impact absorption members were used in the tests illustrated by FIGS. 6A to 6C.

Referring to FIG. 5, an impact test was executed seven times under the first condition, with similar results. That is, maximum impact powers and impact times obtained via the impact tests were similar. This is because the fall member 220 fell onto the impact conversion member 300, i.e., without the impact conversion member 230 therebetween, to from a point impact. As such, the test was made under the same conditions. It is noted, with respect to FIG. 5, that some graphs may not be illustrated due to overlap with other graphs in FIG. 5.

Referring to FIGS. 6A to 6C, results of impact absorption members were obtained via impact tests executed five times under the second condition. FIGS. 6A and 6C are graphs illustrating test results of impact on two-layered absorption members formed of different materials. As shown in FIGS. 6A and 6C, two peak values exist, i.e., corresponding to the two different layers. FIG. 6B is a graph illustrating test results of impact on three-layered absorption members formed of different materials. As shown in FIG. 6B, three peak values exist, i.e., corresponding to the three different layers. As illustrated in FIGS. 6A to 6C, the measuring apparatus according to the inventive concept may measure a distribution of impact powers of multi-layered impact absorption members according to a time lapse. In FIGS. 6A to 6C, some graphs may not be illustrated due to overlap with other graphs.

Figure 7A:
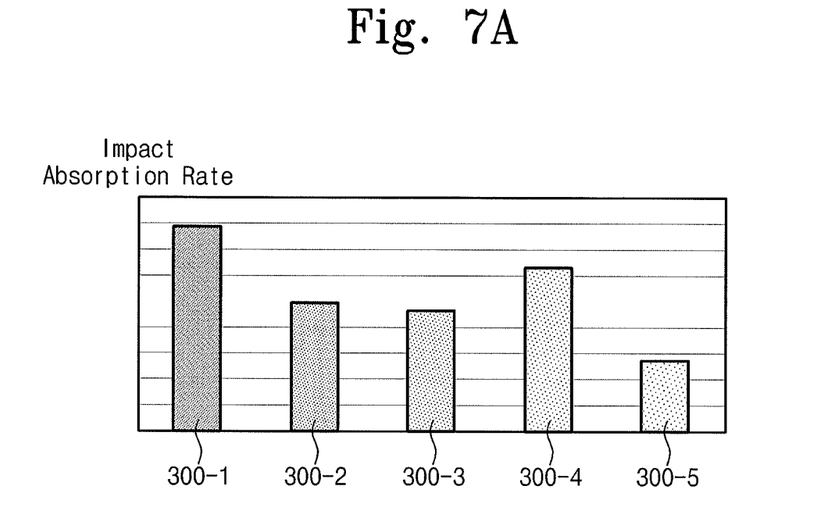
FIG. 7A is a graph illustrating an impact absorption rate of a flat display device measured by a fall test of a display device.
Figure 7B:
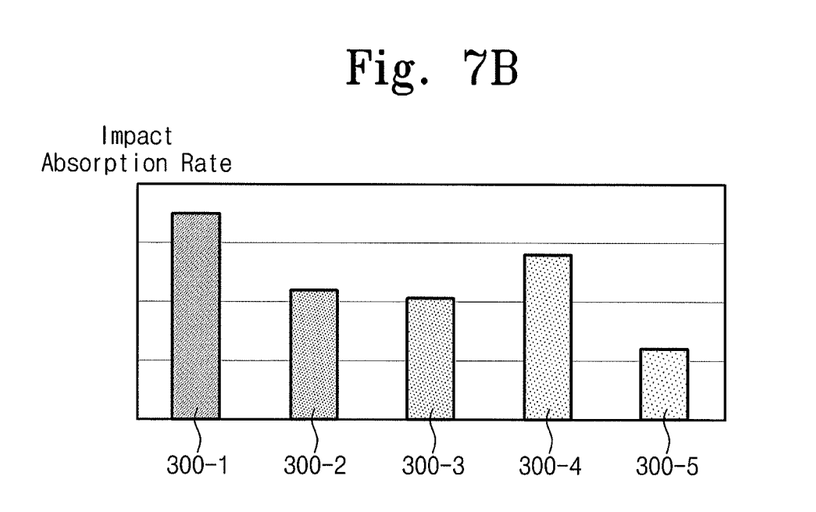
FIG. 7B is a graph illustrating an impact absorption rate of an impact absorption member measured by a measuring apparatus according to an embodiment of the inventive concept.

FIG. 7A is a graph illustrating an impact absorption rate of a flat display device conventionally measured by a fall of a display device. FIG. 7B is a graph illustrating an impact absorption rate of an impact absorption member directly measured by a measuring apparatus according to an embodiment of the inventive concept. As illustrated in FIGS. 7A and 7B, five different impact absorption members 300-1 to 300-5 were measured for an impact absorption rate.

Referring to FIGS. 7A and 7B, a difference between an impact absorption rate calculated by the measuring apparatus 200 according to the inventive concept and an impact absorption rate calculated by a fall test of a display device was small. While an order of impact absorption rates was identical and relative results of impact absorption rates were similar, the actual, i.e., absolute, values of impact absorption rates were different. Thus, the measuring apparatus 200 of the inventive concept may measure an impact absorption rate of the impact absorption member 300 inserted within a display device without a display device.

Figure 8:
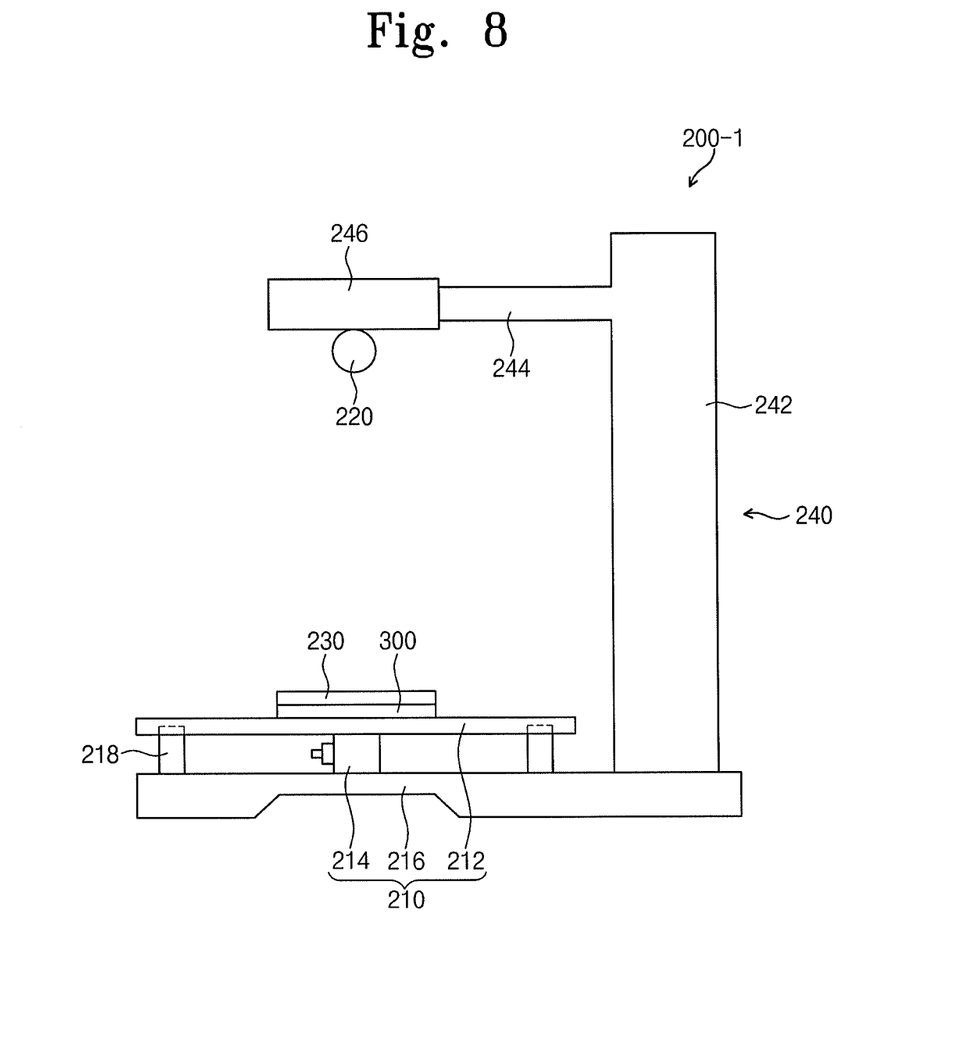
FIG. 8 is a lateral view of an impact absorption rate measuring apparatus according to another embodiment of the inventive concept.
Figure 9A:
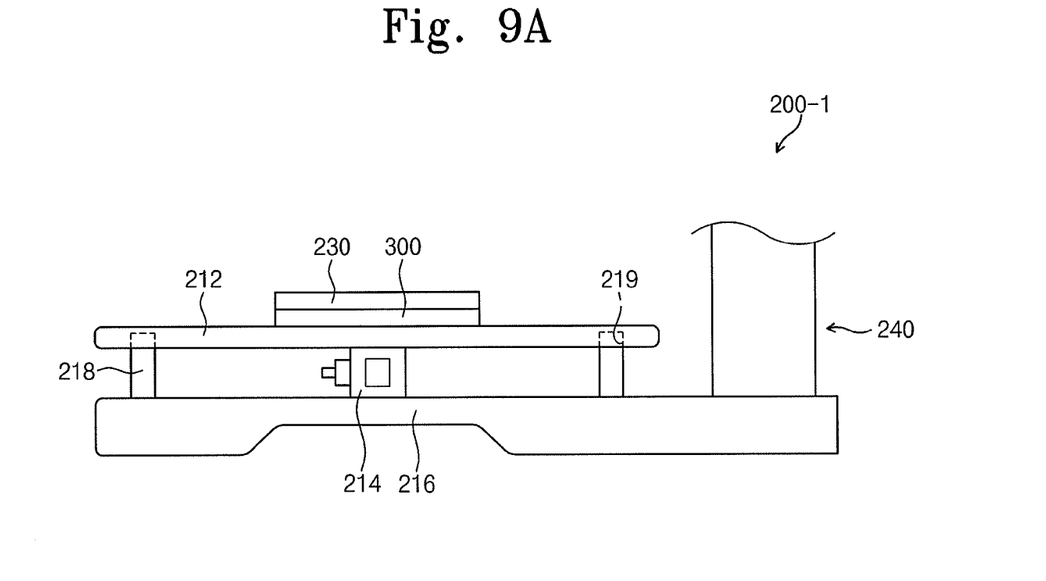
FIGS. 9A and 9B are diagrams schematically illustrating enlarged parts of the impact absorption rate measuring apparatus in FIG. 8.
Figure 9B:
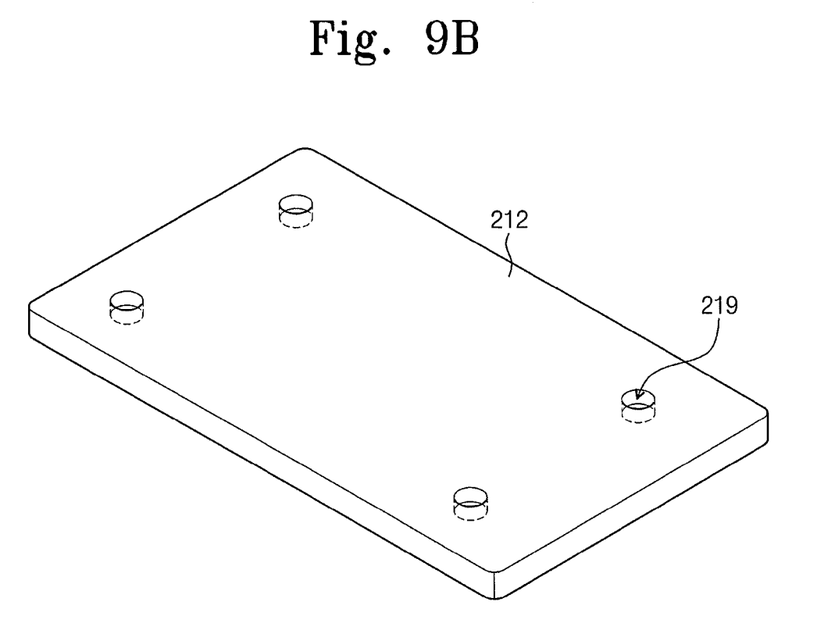

FIG. 8 is a lateral view of an impact absorption rate measuring apparatus according to another embodiment of the inventive concept. FIGS. 9A and 9B are diagrams schematically illustrating a part of an impact absorption rate measuring apparatus in FIG. 8. A measuring apparatus according to another embodiment of the inventive concept will be more fully described with reference to FIGS. 8, 9A, and 9B. In FIGS. 8, 9A, and 9B, description of components that are identical to those in FIG. 3 may be omitted.

As illustrated in FIG. 8, a measuring apparatus 200-1 according to the inventive concept may include a fixing member 240 that is configured to instantly fix the fall member 220 at a height spaced apart from the impact absorption member 230. The fixing member 240 may include a vertical axis portion 242 perpendicular to the second member 216 of the measuring unit 210, a parallel axis portion 244 parallel with the second member 216 and connected to the vertical axis portion 242, and a magnet portion 246 connected to the parallel axis portion 244. During a period of time when an electric field is formed at the magnet portion 246, the fall member 220 may be fixed at the magnet portion 246. In FIG. 8, the vertical axis portion 242 and the parallel axis portion 244 are illustrated as one unit, i.e., formed integrally with each other. However, the inventive concept is not limited thereto, e.g., the parallel axis portion 244 may be attached to the vertical axis portion 242 to be shifted in an up-and-down direction.

The second member 216 of the measuring unit 210 may further include a plurality of protrusion portions 218 provided at a surface facing the first member 212. The protrusion portions 218 may support the first member 212. The protrusion portions 218 may have a bar shape or a cylinder shape.

If the fall member 220 does not fall at a center of the impact conversion member 230, an impact power forced to the impact conversion member 230 may be focused only at a part of the impact conversion member 230. In other words, if the fall member 220 does not impact a center of the impact conversion member 230, the point impact may not properly transform into a surface contact, i.e., may change a contact surface between the impact conversion member 230 and the sensor 214, thereby cause inaccurate test result.

However, as the protrusion portions 218 support the impact conversion member 230, e.g., the impact conversion member may be constantly maintained in parallel to the second member, a contact surface between the impact conversion member 230 and the sensor 214 may be maintained constantly, even if the fall member 220 does not impact the center of the impact conversion member 230.

Referring to FIGS. 9A-9B, the protrusion portions 218 may be disposed at a constant interval, e.g., each protrusion portion 218 may be positioned a constant interval with respect to the sensor 214 to have the sensor 214 at a center. For example, as illustrated in FIGS. 9A and 9B, four protrusion portions 218 may be provided to correspond to corners of the first member 212. However, the number of protrusion portions 218 is not limited thereto.

The first member 212 may have a plurality of groove portions 219 that are formed to partially receive the protrusion portions 218. Although a large impact power may be forced to the impact conversion member 230, the first member 212 may remain connected to the second member 216 via the protrusion portions 218 and the groove portions 219.

Figure 10A:
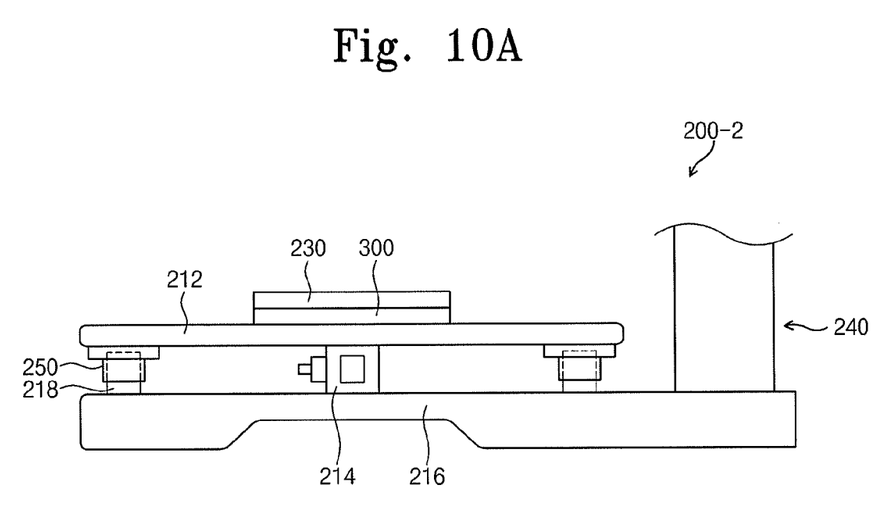
FIGS. 10A and 10B are diagrams partially illustrating an impact absorption rate measuring apparatus according to another embodiment of the inventive concept.
Figure 10B:
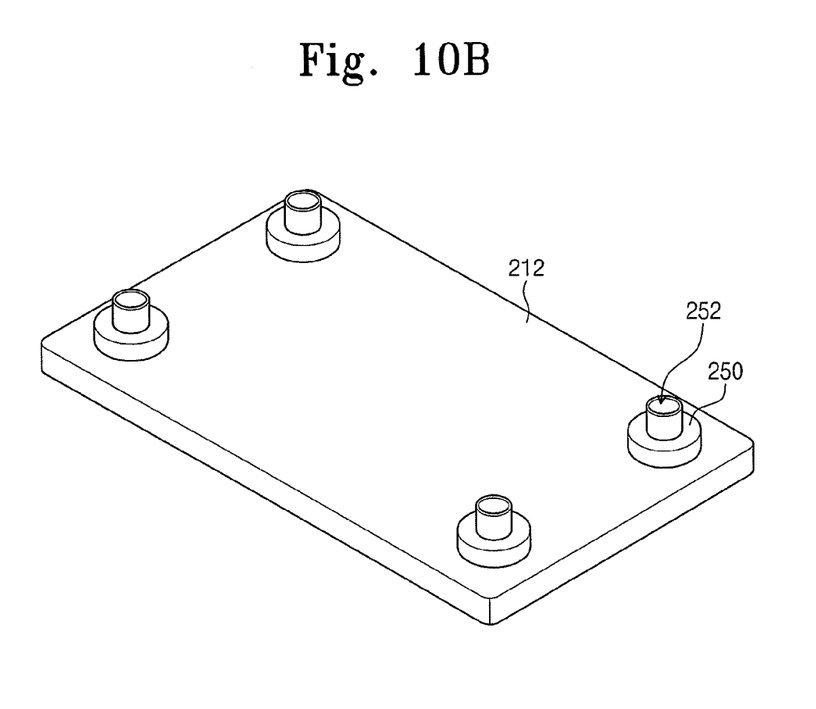

FIGS. 10A and 10B are diagrams partially illustrating an impact absorption rate measuring apparatus according to another embodiment of the inventive concept. In FIGS. 10A and 10B, description of components that are identical to those in FIGS. 3, 8, 9A, and 9B is omitted.

An impact absorption rate measuring apparatus 200-2 according to the inventive concept may include a plurality of receiving members 250. The plurality of receiving members 250 may perform the function of the groove portions 219 illustrated in FIG. 9B.

The receiving members 250 may be attached to a surface of the first member 212 opposite to the second member 216. The receiving members 250 may have groove portions 252, in which protrusion portions 218 are inserted. Since groove portions 219 are not formed at the first member 212, a thickness of the first member 212 may be thin.

The receiving members 250 may provide grooves deeper than groove portions 219 illustrated in FIGS. 9A and 9B. This may enable the first member 212 and the second member 216 to be more securely attached to each other. Nevertheless, an area of the first member 212 supported by the protrusion portions 218 may be identical to that of the impact absorption rate measuring apparatus 200-1 in FIGS. 9A and 9B.

According to the example embodiments, it may be possible to measure an impact absorption rate of an impact absorption member to be inserted into a flat panel display, i.e., independently and separately from the flat display device. That is, it may be possible to reproduce an impact situation generated in a flat display device by converting a point impact into a surface impact. An impact absorption rate reflecting a nearly actual impact situation may be measured under the condition that no impact absorption member is mounted at a flat display device. Further, it is possible to execute an impact absorption rate measuring test operation with a high reliability and a low cost.

The above-disclosed subject matter is to be considered illustrative, and not restrictive, and the appended claims are intended to cover all such modifications, enhancements, and other embodiments, which fall within the true spirit and scope. Thus, to the maximum extent allowed by law, the scope is to be determined by the broadest permissible interpretation of the following claims and their equivalents, and shall not be restricted or limited by the foregoing detailed description.

What is claimed is:

1. An impact absorption rate measuring apparatus, comprising:
    a measuring unit supporting an impact absorption member and measuring an impact absorption rate of the impact absorption member, the measuring unit including:
    a first member supporting the impact absorption member,
    a sensor calculating the impact absorption rate,
    a second member supporting the sensor, the sensor being between the first member and the second member along a vertical direction, and
    a plurality of protrusion portions spaced apart from each other, the protrusion portions extending from the second member to the first member;
    an impact conversion member on the impact absorption member, the impact absorption member being stacked between the measuring unit and the impact conversion member; and
    a fall member falling on an upper surface of the impact conversion member, the upper surface of the impact conversion member facing away from the impact absorption member.

2. The impact absorption rate measuring apparatus of claim 1, wherein the plurality of protrusion portions are spaced apart from each other at a constant interval, the sensor being placed between the protrusions along a horizontal direction.

3. The impact absorption rate measuring apparatus of claim 2, wherein the plurality of protrusion portions are spaced apart from each other along a perimeter of the first member to define an outline, the sensor being in a center of the outline.

4. The impact absorption rate measuring apparatus of claim 2, wherein the first member includes a plurality of groove portions, the protrusion portions being partially inserted into the groove portions, respectively.

5. The impact absorption rate measuring apparatus of claim 2, further comprising a plurality of receiving members on a surface of the first member facing the second member, the protrusion portions being partially inserted into grooves in the receiving members, respectively.

6. The impact absorption rate measuring apparatus of claim 1, wherein the sensor measures an impact power and an impact time to calculate the impact absorption rate.

7. The impact absorption rate measuring apparatus of claim 6, wherein the sensor calculates the impact absorption rate according to the following equation, $$Ir = \frac{Ddt}{Idt} \times \left\{ \frac{(Iif - Dif)}{Iif} \times 100 \right\}$$

wherein Ir is the impact absorption rate, Ddt is an impact time measured when the impact absorption member is not disposed, Idt is an impact time measured when the impact absorption member is disposed, Iif is an impact power measured when the impact absorption member is not disposed, and Dif is an impact power measured when the impact absorption member is disposed.

8. The impact absorption rate measuring apparatus of claim 1, wherein the impact conversion member includes metal.

9. The impact absorption rate measuring apparatus of claim 1, wherein the fall member has a shape to force an impact to the impact conversion member from a point.

10. The impact absorption rate measuring apparatus of claim 9, wherein the fall member has a spherical shape or a hemispherical shape.

11. The impact absorption rate measuring apparatus of claim 1, further comprising a fixing member to temporarily fix the fall member at an upper side of the impact absorption member.

12. The impact absorption rate measuring apparatus of claim 1, wherein the fixing member includes:
    a vertical axis portion perpendicular to the measuring unit;
    a parallel axis portion attached to the vertical axis portion at an upper side of the measuring unit to be parallel with the measuring unit; and
    a magnet portion attached to the parallel axis portion and fixing the fall member.

13. The impact absorption rate measuring apparatus of claim 1, wherein the impact absorption member is directly between the impact absorption member and the impact conversion member, the fall member free falling directly on the upper surface of the impact conversion member.

14. The impact absorption rate measuring apparatus of claim 1, wherein the impact absorption member, the impact conversion member, the first and second members of the measuring unit, and the sensor are parallel to a surface supporting the impact absorption rate measuring apparatus, a force of gravity being normal to the surface supporting the impact absorption rate measuring apparatus.

15. An impact absorption rate measuring apparatus, comprising:
    a first member to support an impact absorption member;
    an impact conversion member on the impact absorption member;
    a fall member to free fall directly on the impact conversion member; and
    a sensor disposed at a lower side of the first member, the sensor measuring an impact absorption rate of the impact absorption member.

16. The impact absorption rate measuring apparatus of claim 15, further comprising a second member, the sensor being between the first and second members.

17. The impact absorption rate measuring apparatus of claim 16, further comprising a plurality of protrusion portions on the second member and spaced apart from each other, the protrusion portions extending from the second member to the first member.

18. The impact absorption rate measuring apparatus of claim 15, wherein the sensor measures an impact power forced to the first member from the fall member and an impact time when the fall member forces an impact to the first member, and calculates the impact absorption rate based on the impact power and the impact time.

19. The impact absorption rate measuring apparatus of claim 15, wherein the impact absorption member, the impact conversion member, the first member, and the sensor are parallel to a surface supporting the impact absorption rate measuring apparatus, a force of gravity being normal to the surface supporting the impact absorption rate measuring apparatus.

20. The impact absorption rate measuring apparatus of claim 15, wherein the sensor includes a first surface contacting the first member and a second surface opposite the first surface, the first surface of the sensor having an area that equals to or is smaller than the second surface of the sensor.

* * * * *